US00PP20069P2

(12) United States Plant Patent
Hartman

(10) Patent No.: US PP20,069 P2
(45) Date of Patent: Jun. 9, 2009

(54) *CALADIUM* PLANT NAMED 'RASPBERRY MOON'

(50) Latin Name: *Caladium×hortulanum*
Varietal Denomination: Raspberry Moon

(76) Inventor: Robert Dale Hartman, 158 Blue Moon Ave., Lake Placid, FL (US) 33852

( * ) Notice: Subject to any disclaimer, the term of this patent is extended or adjusted under 35 U.S.C. 154(b) by 0 days.

(21) Appl. No.: 12/070,568

(22) Filed: Feb. 19, 2008

(51) Int. Cl.
*A01H 5/00* (2006.01)

(52) U.S. Cl. ..... Plt./373
(58) Field of Classification Search ..... Plt./373
See application file for complete search history.

*Primary Examiner*—June Hwu
(74) *Attorney, Agent, or Firm*—C. A. Whealy

(57) ABSTRACT

A new and distinct cultivar of *Caladium* plant named 'Raspberry Moon', characterized by its tall and upright plant habit; vigorous and dense growth habit; fancy-type leaves that are light green-colored with random dark green and red-colored spots and splotches.

4 Drawing Sheets

Botanical designation: *Caladium×hortulanum.*
Cultivar denomination: 'RASPBERRY MOON'.

BACKGROUND OF THE INVENTION

The present invention relates to a new and distinct cultivar of *Caladium* plant, botanically known as *Caladium× hortulanum,* commercially referred to as a fancy leaf-type *Caladium* and hereinafter referred to by the name 'Raspberry Moon'.

The objective of the Inventor's breeding program is to create new *Caladium* cultivars that have uniform plant habit, exceptional performance and attractive foliage coloration.

The new *Caladium* originated from a cross-pollination made by the Inventor in June, 2002, in Lake Placid, Fla. of the *Caladium×hortulanum* cultivar Miss Muffet, not patented, as the female, or seed, parent with the *Caladium× hortulanum* cultivar Fire Chief, not patented, as the male, or pollen, parent. The new *Caladium* was discovered and selected by the Inventor as a single plant within the progeny of the stated cross-pollination in a controlled environment in Lake Placid, Fla. on Jun. 15, 2003.

Asexual reproduction of the new cultivar by tuber divisions in a controlled environment in Lake Placid, Fla. since Apr. 15, 2004 has shown that the unique features of this new *Caladium* are stable and reproduced true to type in successive generations of asexual reproduction.

SUMMARY OF THE INVENTION

The cultivar Raspberry Moon has not been observed under all possible environmental conditions. The phenotype may vary somewhat with variations in environment such as temperature and light intensity, without, however, any variance in genotype.

The following traits have been repeatedly observed and are determined to be the unique characteristics of 'Raspberry Moon'. These characteristics in combination distinguish 'Raspberry Moon' as a new and distinct cultivar of *Caladium:*

1. Tall and upright plant habit.
2. Vigorous and dense growth habit.

3. Fancy-type leaves that are light green-colored with random dark green and red-colored spots and splotches.

Plants of the new *Caladium* differ from plants of the female parent, the cultivar Miss Muffet, in the following characteristics:

1. Plants of the new *Caladium* are not as compact as plants of the cultivar Miss Muffet.
2. Plants of the new *Caladium* are fancy leaf-types whereas plants of the cultivar Miss Muffet are strap leaf-types.
3. Leaves of plants of the new *Caladium* have more red spots and splotches than leaves of plants of the cultivar Miss Muffet.

Plants of the new *Caladium* differ from plants of the male parent, the cultivar Fire Chief, primarily in leaf color as leaves of plants of the cultivar Fire Chief were dark green in color with random red-colored spots and splotches.

Plants of the new *Caladium* can also be compared to plants of the cultivar Florida Beauty, not patented. In side-by-side comparisons conducted in Lake Placid, Fla., plants of the new *Caladium* differed from plants of the cultivar Florida Beauty in the following characteristics:

1. Plants of the new *Caladium* were taller and more vigorous than plants of the cultivar Florida Beauty.
2. Leaves of plants of the new *Caladium* were more elongate than and not as rounded as leaves of plants of the cultivar Florida Beauty.
3. Leaves of plants of the new *Caladium* were more undulate than and not as smooth as leaves of plants of the cultivar Florida Beauty.
4. Plants of the new *Caladium* and the cultivar Florida Beauty differed in leaf coloration as plants of the cultivar Florida Beauty had olive-colored leaves with red-colored spots and splotches.

BRIEF DESCRIPTION OF THE PHOTOGRAPHS

The accompanying photographs illustrate the overall appearance of the new *Caladium.* These photographs show the colors as true as it is reasonably possible to obtain in colored reproductions of this type. Colors in the photographs may differ slightly from the color values cited in the detailed botanical description which accurately describe the colors of the new *Caladium*.

The photograph on the first sheet is a side perspective view of a typical plant of 'Raspberry Moon' grown in a container in a shadehouse.

The photograph on the second sheet comprises a close-up view of a typical leaf of 'Raspberry Moon' grown in a shadehouse.

The photograph at the top of the third sheet is a side perspective view of typical plants of 'Fire Chief' (left), 'Raspberry Moon' (center) and 'Miss Muffet' (right) grown in a shadehouse.

The photograph at the bottom of the third sheet is a side perspective view of typical plants of 'Florida Beauty' (left) and 'Raspberry Moon' (right) grown in a shadehouse.

The photograph at the top of the fourth sheet is a top perspective view of typical plants of 'Raspberry Moon' grown in an outdoor nursery.

The photograph at the bottom of the fourth sheet is a close-up view of typical leaf petioles, tubers and roots of 'Raspberry Moon'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in 15-cm containers in Avon Park, Fla. during the spring in a polypropylene-covered shadehouse and plants grown in ground beds in Zolfo Springs, Fla. during the late summer in an outdoor nursery. All plants were grown under conditions and practices which approximate those generally used in commercial *Caladium* production. During the production of the plants, day temperatures ranged from about 20° C. to 35° C., night temperatures ranged from about 10° C. to 20° C. and light levels were about 8,000 foot-candles (shadehouse) or 10,000 to 12,000 foot-candles (outdoor nursery). Plants grown in the shadehouse were about seven weeks from planting tubers when the photographs and the detailed description were taken. Plants grown in the outdoor nursery were about seven months from planting tuber pieces when the photographs and the detailed description were taken.

Botanical classification: *Caladium×hortulanum* cultivar Raspberry Moon.

Parentage:

*Female, or seed, parent.*—*Caladium×hortulanum* cultivar Miss Muffet, not patented.

*Male, or pollen, parent.*—*Caladium×hortulanum* cultivar Fire Chief, not patented.

Propagation:

*Type.*—By tubers and by tuber divisions.

*Time to initiate roots, summer.*—About seven to ten days at 32° C.

*Time to initiate roots, winter.*—About two to three weeks at 24° C.

*Tuber description.*—Number of buds per tuber, shadehouse-grown plants: About 14 actively growing buds/shoots. Number of buds per tuber, outdoor nursery-grown plants: About three actively growing buds/shoots. Height: About 2.7 cm. Diameter: About 5.7 cm. Texture: Thick, starchy; somewhat brittle. Color: Epidermis, between N199D to 199A; interior, 4C to 4D. Root description/habit: Dense, thick and white fleshy roots.

Plant description:

*Plant type.*—Herbaceous perennial.

*Plant/growth habit.*—Tall and upright plant habit; inverted triangle. Vigorous, dense growth habit; suitable for 15-cm to 25-cm containers. Leaf petioles arising from tubers; petioles mostly upright and arching with development.

*Plant height, from soil level to top of leaf plane, shadehouse-grown plants.*—About 33 cm to 39 cm.

*Plant height, from soil level to top of inflorescences, shadehouse-grown plants.*—About 42 cm.

*Plant diameter or spread, shadehouse-grown plants.*—About 46 cm.

*Plant height, from soil level to top of leaf plane, outdoor nursery-grown plants.*—About 47 cm to 50 cm.

*Plant height, from soil level to top of inflorescences, outdoor nursery-grown plants.*—Inflorescences not observed on plants grown in the outdoor nursery.

*Plant diameter or spread, outdoor nursery-grown plants.*—About 50 cm to 56 cm.

*Cataphylls* (*only observed on shadehouse-grown plants*).—Length: About 5 cm to 11 cm. Width: About 2 cm. Shape: Linear. Apex: Acute. Base: Sheathing the stem. Color, inner and outer surfaces: Between N170D and 49D; streaks, N186A variably tinged with 147B; occasionally entirely N186A. With development, color becoming closer to 200A tinted with 187A.

Foliage description:

*Length, shadehouse-grown plants.*—About 22 cm to 24.5 cm.

*Width, shadehouse-grown plants* (*flattened*).—About 15 cm to 17 cm.

*Length, outdoor nursery-grown plants.*—About 18 cm to 23.5 cm.

*Width, outdoor nursery-grown plants* (*flattened*).—About 12 cm to 14 cm.

*Shape.*—Ovate.

*Apex.*—Acute.

*Base.*—Sagittate to peltate.

*Margin.*—Entire; some broad undulate.

*Texture, upper surface.*—Smooth, glabrous.

*Texture, lower surface.*—Smooth, glabrous; glaucous.

*Venation pattern.*—Pinnate-palmate.

*Color, shadehouse-grown plants.*—Developing leaves, upper surface: Ground: 147C to 147D with 145D cast. Margins: Thin, 187B; basal notch, 59A. Center: Random spots and splotches, 59B, 60A to 60B, 185B and 184B to 184C. Venation: Midrib, 56D variably marked with 60B; primary veins, 59B and 56D; junction of midrib and primary veins, N186C. Developing leaves, lower surface: Ground: 138B and 145D. Margins: Thin, 187B; basal notch, 187B. Center: Random spots and splotches, 59B to 59C and 185B to 185C. Venation: Midrib and primary veins, 145D tinged with 150D. Fully developed leaves, upper surface: Ground: 147D with 145B cast and random areas of 145D, 147A and 137A. Margins: Thin, 187B; basal notch, 60A. Center: Random spots and splotches, 59B, 60A to 60B and 185B to 185C. Venation: Midrib, 145D flushed and streaked with 187D; primary veins, 187C and 59C; junction of midrib and primary veins, N186C. Fully developed leaves, lower surface: Ground: 147D with 138B cast. Margins: Thin, 187B; basal notch, 187B. Center: Random spots and splotches, 59A, 185B and 185C. Venation: Midrib and primary veins, 145D with 195D cast and faintly tinged with 182C.

*Color, outdoor nursery-grown plants.*—Developing leaves, upper surface: Ground: 137B to 137C and 145D. Margins: Thin, 59A; basal notch, 59A. Center: Random spots and splotches, 53A, 60A to 60B. Venation: Midrib and primary veins, 147A or 187A; junction of midrib and primary veins, 59A. Developing leaves, lower surface: Ground: 147B to 147C, 138B and 145D. Margins: Thin, 187A; basal notch, 187A. Center: Random spots and splotches, 59A to 59B, 59B to 59C and 59C to 59D. Venation: Midrib, 195B tinged with 182D; primary veins, 195B with 137B faintly tinged with 182D. Fully developed leaves, upper surface: Ground: Between 146C to 144A with 137D cast; random areas of 139A, 145C, 137B to 137C, 146C and 144A. Margins: Thin, 59A; basal notch, 59A. Center: Random spots and splotches, 53A, 60A and 60B to 60C. Venation: Midrib and primary veins, proximal, 183A, and distal, between 144A and 146A; junction of midrib and primary veins, 59A. Fully developed leaves, lower surface: Ground: 147B to 147C with 138B cast. Margins: Thin, 187B; basal notch, 187B. Center: Random spots and splotches, 145D, 59A, 59C to 59D and 60C to 60D. Venation: Midrib and primary veins, 195B tinged with 182D.

*Petiole.*—Aspect: Mostly erect, outwardly arching with development. Length, shadehouse-grown plants: About 24 to 34 cm. Diameter, distal, shadehouse-grown plants: About 4.5 mm. Diameter, proximal, shadehouse-grown plants: About 1 cm. Length, outdoor nursery-grown plants: About 41 cm to 54 cm. Diameter, distal, outdoor nursery-grown plants: About 5 mm. Diameter, proximal, outdoor nursery-grown plants: About 7 mm. Strength: Strong; flexible. Color, distal, shadehouse-grown plants: Between 182D and N170D variably streaked with N186A. Color, proximal, shadehouse-grown plants: N170D variably streaked with N186A; often tinged with 147B. Color, distal and proximal, outdoor nursery-grown plants: Between N170D to 49D variably streaked with N186B to N186C. Wing length, shadehouse-grown plants: About 6.3 cm. Wing diameter, shadehouse-grown plants: About 7 mm. Wing length, outdoor nursery-grown plants: About 9.2 cm. Wing diameter, outdoor nursery-grown plants: About 1 cm. Wing color, shadehouse-grown plants: N170D, streaked with N186A and variably tinged with 147B. Wing color, outdoor nursery-grown plants: Between N170D and 49D streaked with N186B to N186C.

Inflorescence description: Inflorescences only observed on shadehouse-grown plants.

*Inflorescence arrangement.*—Upright hooded spathes surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers develop between female and male flower zones; near this area, the spathe constricts surrounding the female flowers.

*Fragrance.*—None detected.

*Natural flowering season/longevity.*—Plants of the new *Caladium* typically flower during the spring or early summer in central Florida. Flowers develop about eight weeks after growth commences. Inflorescences last about three days before fading; inflorescences persistent.

*Spathe.*—Length: About 12 cm. Width, distal: About 5.2 cm. Width, proximal: About 3.3 cm. Shape: Ovate. Apex: Acuminate. Base: Tapering. Margin: Entire. Texture, upper and lower surfaces: Smooth, glabrous. Color: Front surface: Upper two-thirds: 155B to 155C tinged with 184A to 184B and 185C. Color becoming closer to 199C to 199D with development. Lower one-third: 147B to 147C with streaks of 155C and occasionally tinged with 185D; at the base, N186C. Color becoming closer to 147A to 147B with streaks of 145D with development. Rear surface: Upper two-thirds: Variable, 157A and 155C with random areas of 145B to 145C and variably marked with 185B and 186D. Lower one-third: 147B with streaks of 193D and occasionally tinged with 185D. Spadix: Length, entire spadix; About 10 cm. Length, male flower zone: About 5.4 cm. Length, sterile flower zone: About 2.4 cm. Length, female flower zone: About 2.2 cm. Diameter, male flower zone: About 1.2 cm. Diameter, sterile flower zone: About 8 mm. Diameter, female flower zone: About 1 cm. Shape: Columnar. Apex: Obtuse. Base: Obtuse. Aspect: Upright. Color, mature, male zone: 159C to 159D. Color, mature, sterile zone: 159C to 159D Color, mature, female zone: 161C to 161D. Male flowers: Quantity per spadix: About 236. Shape: Obovate. Height: About 3 mm. Diameter: About 3 mm. Anther color: Close to 157D. Amount of pollen: Moderate. Pollen color: 158A. Female flowers: Quantity per spadix: About 285. Shape: Obovate. Height: About 2 mm. Diameter: About 1.2 mm. Stigma color: 161C to 161D. Ovary color: 155D. Scape: Length: About 30 cm. Diameter: About 8 mm. Strength: Sturdy; flexible. Aspect: Erect. Texture: Smooth, glabrous; glaucous. Color: N170D variably streaked with N186A; at the spathe, 147B.

*Seed and fruit.*—Seed and fruit development has not been observed on plants of the new *Caladium.*

Disease/pest resistance: Plants of the new *Caladium* have been observed to be somewhat tolerant to Pythium root rot and Xanthomonas leaf spot. Plants of the new *Caladium* have not been observed to be resistant to pests or other pathogens common to *Caladium.*

Temperature tolerance: Plants of the new *Caladium* have been observed to be tolerant to temperatures ranging from about 7° C. to about 40° C.

It is claimed:

1. A new and distinct *Caladium* plant named 'Raspberry Moon' as illustrated and described.

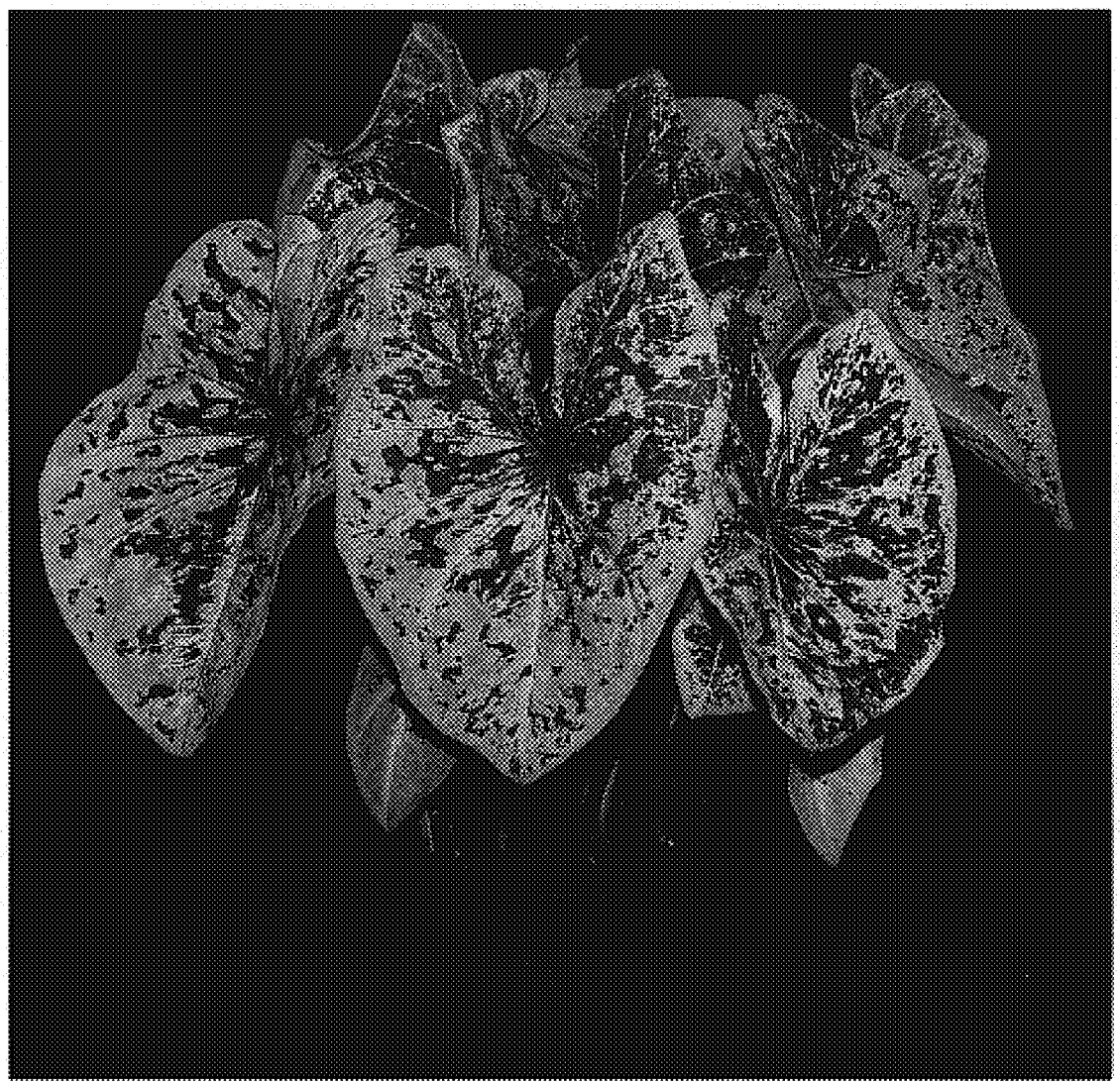

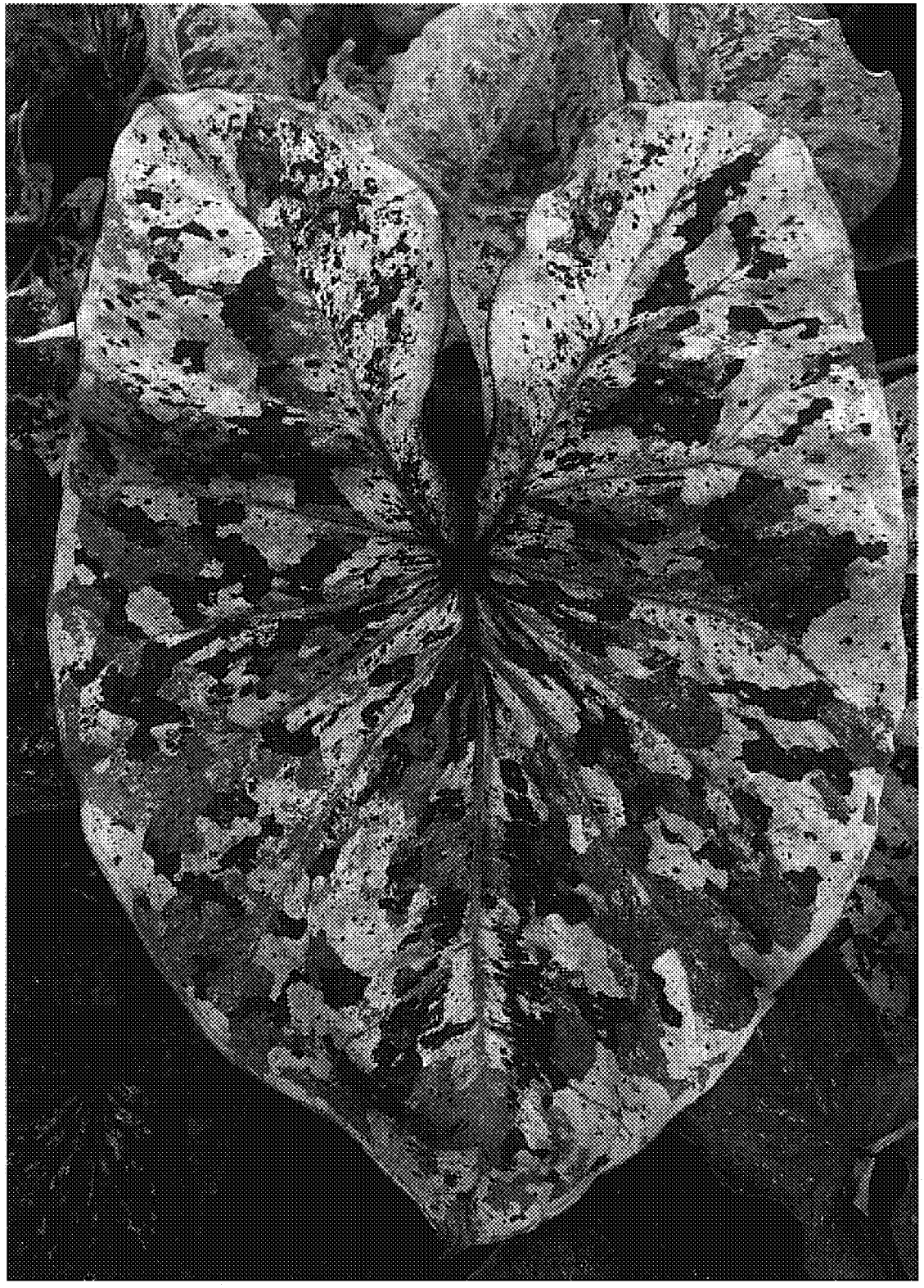

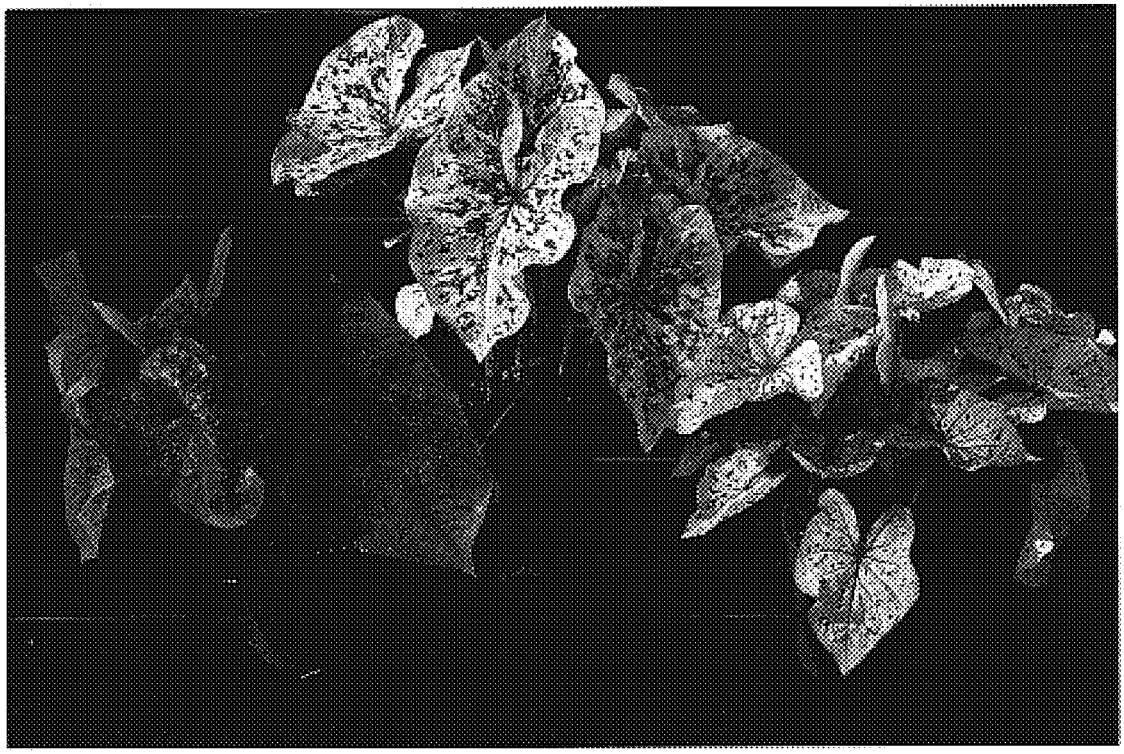
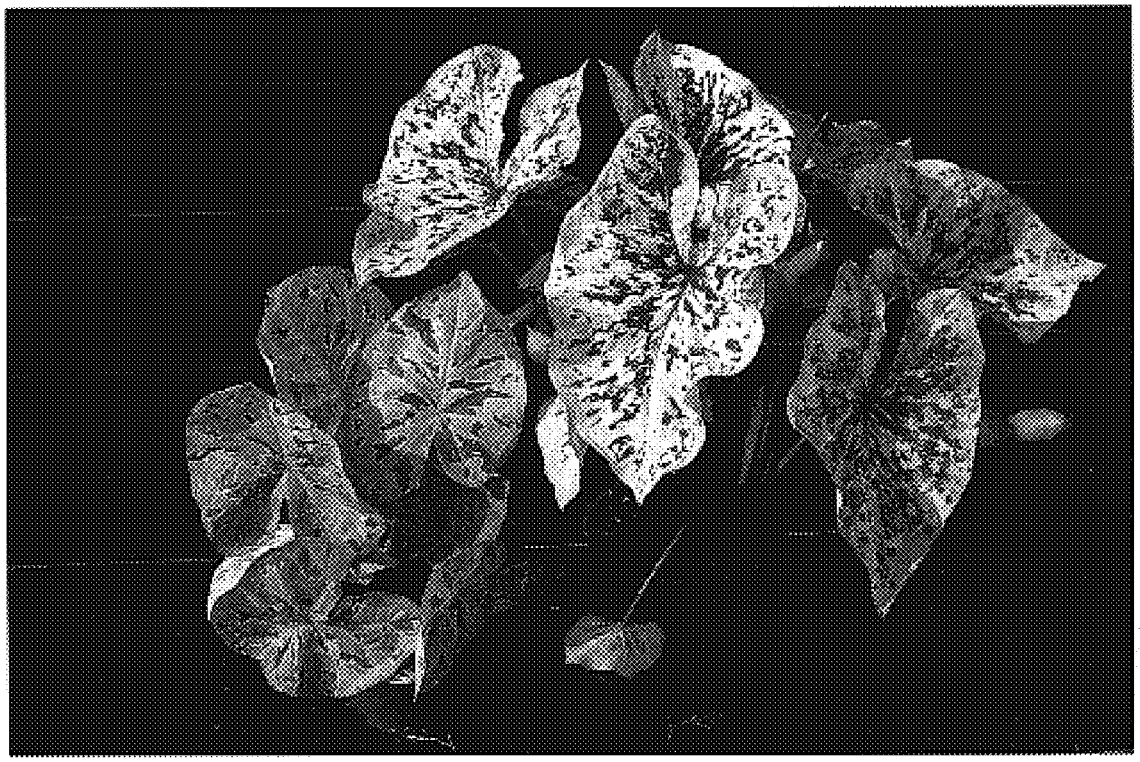

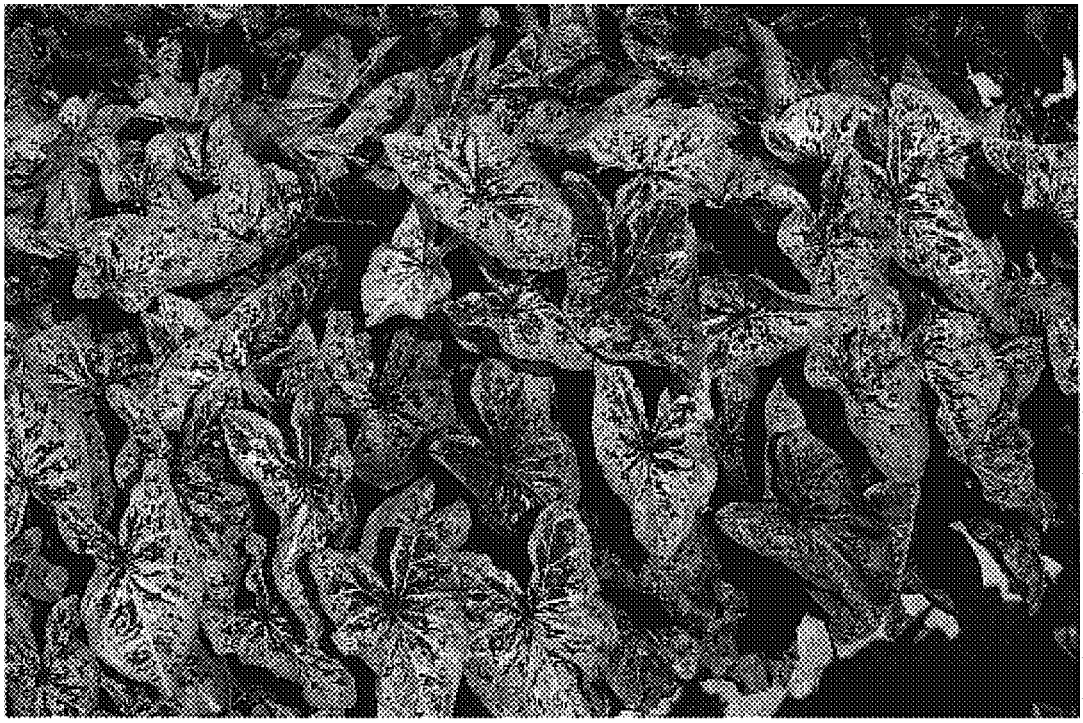
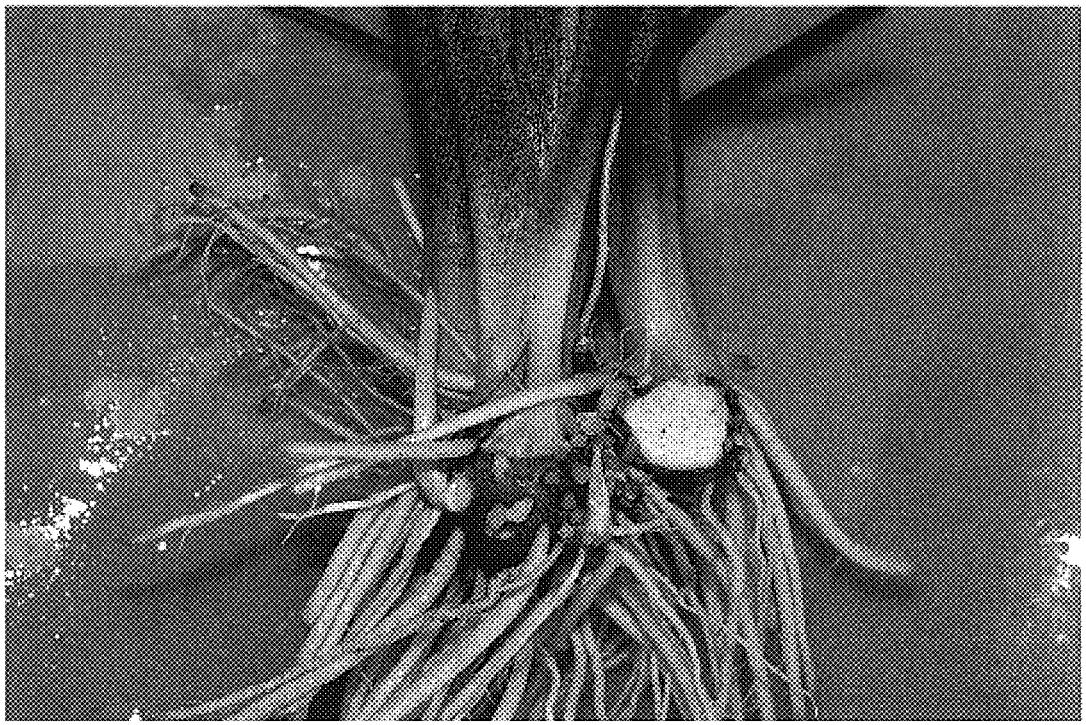

* * * * *